United States Patent [19]

Barth

[11] 4,356,174

[45] Oct. 26, 1982

[54] BETA-LACTAMASE INHIBITING 2-BETA-SUBSTITUTED-2-ALPHA-METHYL-(5R)PENAM-3-ALPHA-CARBOXYLIC ACID 1,1-DIOXIDES AND INTERMEDIATES THEREFOR

[75] Inventor: Wayne E. Barth, East Lyme, Conn.

[73] Assignee: Pfizer Inc., New York, N.Y.

[21] Appl. No.: 301,995

[22] Filed: Sep. 14, 1981

[51] Int. Cl.$^3$ ............... A61K 31/43; A61K 31/425; C07D 499/68; C07D 513/04
[52] U.S. Cl. .............................. 424/114; 260/239.1; 260/245.2 R; 424/270; 424/271
[58] Field of Search .............. 260/245.2 R, 239.1; 424/270, 271, 114

[56] References Cited

U.S. PATENT DOCUMENTS

| | | | |
|---|---|---|---|
| 4,234,579 | 11/1980 | Barth | 424/246 |
| 4,241,050 | 12/1980 | Barth | 424/114 |
| 4,244,951 | 1/1981 | Bigham | 424/250 |
| 4,256,733 | 3/1981 | Barth | 424/114 |
| 4,287,181 | 9/1981 | Kellogg | 424/114 |

FOREIGN PATENT DOCUMENTS 1541832  3/1979  United Kingdom ............ 499/44

OTHER PUBLICATIONS

Cooper, J. Am. Chem. Soc. 94, 1018 (1972).

Primary Examiner—Mary C. Lee
Attorney, Agent, or Firm—Charles J. Knuth; Albert E. Frost; Peter C. Richardson

[57] ABSTRACT

Beta-lactamase inhibiting 2-beta-substituted-2-alpha-methyl-(5R)penam-3-alpha-carboxylic acid 1,1-dioxides and esters thereof, wherein the 2-beta-substituent is cyano, acetyl, alkoxycarbonyl, omegahydroxyalkoxycarbonyl, carbalkoxymethoxycarbonyl or dialkylaminocarbonyl; intermediates therefor wherein the 2-beta-substituent is carboxy, chlorocarbonyl or aminocarbonyl; methods for their preparation and use as beta-lactamase inhibitors.

14 Claims, No Drawings

BETA-LACTAMASE INHIBITING 2-BETA-SUBSTITUTED-2-ALPHA-METHYL-(5R)PENAM-3-ALPHA-CARBOXYLIC ACID 1,1-DIOXIDES AND INTERMEDIATES THEREFOR

BACKGROUND OF THE INVENTION

Efforts to develop beta-lactam antibiotics; i.e., penicillins and cephalosporins, having improved efficacy, particularly against gram-negative and beta-lactam resistant organisms has progressed along several paths. The first is directed to chemical modification of the substituent groups on the basic penam or cepham nucleus, especially of the amino groups at the 6- and 7-positions, respectively, of said nuclei. A second path is aimed at modification of the basic beta-lactam nuclei of said antibiotics. More recently, attention has focused on physical and chemical combinations of a beta-lactam antibiotic with a beta-lactamase inhibitor; i.e., a substance which inhibits beta-lactamases and, as a result, prevents their degrading the beta-lactam ring of said antibiotics to products devoid of antibacterial activity.

Several 6-beta-substituted penicillanic acids and esters thereof wherein the 6-beta-substituent is fluoro, chloro, iodo, alkoxy or alkylmercapto, and S-oxides of said compounds, are described in Belgium Pat. No. 882,027, granted Sept. 3, 1980. Penicillanic acid 1,1-dioxide and esters thereof readily hydrolyzable in vivo and useful as antibacterial agents and beta-lactamase inhibitors are disclosed in U.S. Pat. No. 4,234,579, issued Nov. 18, 1980; and beta-lactamase inhibiting 2-beta-acetoxymethyl penicillanic acid 1,1-dioxide and esters thereof readily hydrolyzable in vivo, and intermediates therefor, are described in U.S. Pat. No. 4,256,733, issued Mar. 17, 1981.

Various 2-beta-methylenepenam derivatives have been reported including halo- [Kukolja et al., J. Am. Chem. Soc., 97, 3192 (1975); Kamiya et al., Tetrahedron Lett., 3001 (1973)]; alkoxy, sulfides, azido and substituted amino (U.S. Pat. No. 3,954,732). Cooper, J. Am. Chem. Soc., 94, 1018 (1972) reported the synthesis of 2-beta-(hydroxymethyl)penicillin 1-beta-oxide. Spry, J. Org. Chem., 44, 3084 (1979) described the synthesis of 2-beta-(hydroxymethyl)penicillin and of 2-beta-(chloroacetoxymethyl)penicillin. In each of these references, the compounds were investigated primarily as intermediates. The compounds 2-beta-(hydroxymethyl)penicillin and its 1-oxide were reported by Spry (loc. cit.) to be biologically less active than the parent penicillin.

Bis-esters of alkanediols with penicillins and penicillanic acid 1,1-dioxide useful, because of their tendency to hydrolyze in vivo to provide both a penicillin and a beta-lactamase inhibitor, as antibacterial agents against beta-lactamase producing bacteria are described in U.S. Pat. No. 4,244,951, issued Jan. 13, 1981, and in British Patent Application No. 2,044,255A, published Oct. 15, 1980. Co-pending U.S. Application Ser. No. 236,407, filed Feb. 20, 1981 describes bis-esters of alkanediols with 6-acyl amidopenicillanic acid and 2-beta-acetoxymethyl-2-alpha-methyl-(5R)penam-3-alpha-carboxylic acid 1,1-dioxide as antibacterial agents. Belgian Pat. No. 885,389, published Mar. 25, 1981, describes bis-esters of alkanediols with penicillins and 2-beta-acetoxymethyl-2-alpha-methyl-(5R)penam-3-alpha-carboxylic acid 1,1-dioxide useful for the same purpose. Several antibacterially active 2-substituted penam derivatives wherein the 2-position substituents, A and B, are A=hydrogen, acyl, alkoxycarbonyl; B=acyl, nitrile, alkoxycarbonyl; and the 6-position substituent is acylamino, tritylamino or amino, are characterized in British Pat. No. 1,541,832, published Mar. 7, 1979. U.S. Pat. No. 4,241,050, issued Dec. 23, 1980, makes known penam 3-carboxylic acid, 1,1-dioxide, and esters thereof, optionally having a methyl group at the 2-position, as beta-lactamase inhibitors.

SUMMARY OF THE INVENTION

New beta-lactamase inhibiting agents of formula I

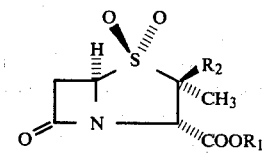

wherein $R_1$ is selected from the group consisting of
(a) hydrogen;
(b) ester forming residues readily hydrolyzable in vivo selected from the group consisting of
(1) 3-phthalidyl, 4-crotonolactonyl and gamma-butyrolacton-4-yl;

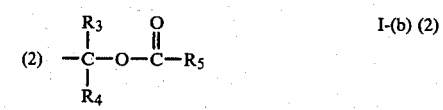

wherein each of $R_3$ and $R_4$ is selected from the group consisting of hydrogen and methyl; and $R_5$ is selected from the group consisting of alkyl having from 1 to 5 carbon atoms and alkoxy having from 1 to 5 carbon atoms; and

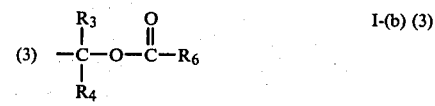

wherein each of $R_3$ and $R_4$ is selected from the group consisting of hydrogen and methyl;

and $R_6$ is

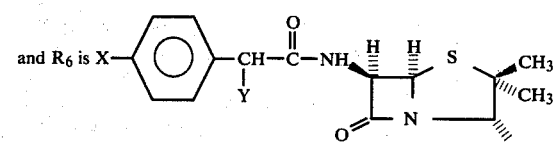

wherein X is selected from the group consisting of hydrogen and hydroxy; and Y is selected from the group consisting of azido and amino;
(c) carboxy protecting group selected from the group consisting of benzyl and 4-nitrobenzyl; $R_2$ is selected from the group consisting of CN or CO-Z; Z is selected from the group consisting of alkoxy having from 1 to 4 carbon atoms; omega-hydroxyalkoxy having from 2 to 4 carbon atoms; carboalkoxymethoxy having from 3 to 6 carbon atoms; dialkylamino wherein each alkyl group has from 1 to 4 carbon atoms; omega-acetoamidoalkoxy having from 2 to 4 carbon atoms in the alkoxy group, and methyl; or a pharmaceutically-acceptable base salt of those compounds wherein $R_1$ is hydrogen; or a pharmaceutically-acceptable acid addition salt of those compounds wherein Y is amino.

Also included in this invention are compounds of formula II

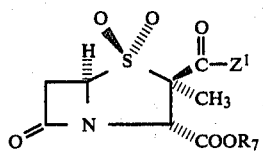

wherein $Z^1$ is selected from the group consisting of chloro, amino, hydroxy and OM wherein M is selected from the group consisting of sodium, potassium, ammonium and n-tetrabutylammonium; and $R_7$ is selected from the group consisting of benzyl and 4-nitrobenzyl, said compounds being useful as intermediates for preparation of compounds of formula I.

By the term "pharmaceutically-acceptable base salt" is meant salt formed with inorganic and organic bases such as ammonia, organic amines, quaternary hydroxides, alkali metal hydroxides, carbonates, bicarbonates, hydrides and alkoxides, as well as alkaline earth metal hydroxides, carbonates, hydrides and alkoxides. Representative examples of such bases are primary amines, such as n-propylamine, n-butylamine, aniline, cyclohexylamine, benzylamine and octylamine; secondary amines, such as diethylamine, morpholine, pyrrolidine and piperidine, tertiary amines, such as triethylamine, N-ethylpiperidine, N-methylmorpholine, N,N-dibenzylethylenediamine and 1,5-diazabicyclo[4.3.0]non-5-ene; quaternary hydroxides such as n-tetrabutylammonium hydroxide; hydroxides, such as sodium hydroxide, potassium hydroxide, ammonium hydroxide and barium hydroxide; alkoxides, such as sodium ethoxide and potassium ethoxide; hydrides, such as calcium hydride and sodium hydride; carbonates, such as potassium carbonate and sodium carbonate; bicarbonates, such as sodium bicarbonate and potassium bicarbonate; and alkali metal salts of long-chain fatty acids, such as sodium 2-ethylhexanoate, and which are non-toxic at the dose levels at which the formula I compounds are used.

By the term "pharmaceutically-acceptable acid addition salt" is meant salts formed with pharmaceutically-acceptable inorganic and organic acids such as hydrochloric, sulfuric, hydrobromic, hydriodic, phosphoric, acetic, citric, ascorbic, tartaric, benzoic, fumaric, maleic, malic, glycolic and mandelic acids.

The term "ester-forming residues readily hydrolyzable in vivo" is here intended to refer to non-toxic ester residues which are rapidly cleaved in mammalian blood or tissue, to release the corresponding free acid (i.e., the compound of formula I, wherein $R_1$ is hydrogen). Typical examples of such readily hydrolyzable ester-forming residues which can be used for $R_1$ are 3-phthalidyl, 4-crotonolactonyl and gamma-butyrolacton-4-yl; bis-esters of alkane-1,1-diols in which one hydroxy group of said diol is esterified with the carboxy group of a compound of formula I, and the other hydroxy group is esterified with a $(C_{2-6})$ alkanoic acid, a $(C_{2-6})$alkyl chloroformate or a 6-acylaminopenicillanic acid. Representative values of $R_1$ in such bis-esters are alkanoyloxymethyl having from 3 to 7 carbon atoms, 1-(alkanoyloxy)ethyl having from 4 to 8 carbon atoms, 1-methyl-1-(alkanoyloxy)ethyl having from 5 to 9 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, 6-(2-amino-2-phenylacetamido)penicillanoyloxymethyl and 6-(2-amino-2-[4-hydroxyphenyl]acetamido)penicillanoyloxymethyl. Preferred readily hydrolyzable ester-forming residues are pivaloyloxymethyl, 1-(ethoxycarbonyloxy)ethyl, 6-(2-amino-2-phenylacetamido)penicillanoyloxymethyl and phthalidyl.

Favored because of their greater activity relative to that of other compounds having formula I as described herein, are those formula I compounds wherein $R_1$ is hydrogen, sodium, potassium, or an ester group readily hydrolyzable in vivo. Preferred compounds are those formula I compounds wherein $R_1$ is hydrogen, sodium or potassium; and $R_2$ is CN, or CO-Z wherein Z is $(C_{1-4})$alkoxy especially the compound wherein Z is methoxy.

DETAILED DESCRIPTION OF THE INVENTION

The compounds of this invention (formulae I and II) are referred to throughout the specification as derivatives of (5R)penam. The term "(5R)penam" refers to the structural formula (III)

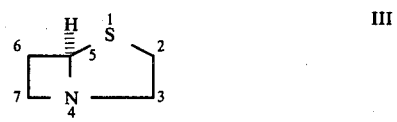

When depicting derivatives of structure III, the bicyclic ring system is understood to substantially be in the plane of the paper. Broken line attachment of a group to the ring system III, indicates that the group is attached from below the plane of the paper, and such a group is said to be in the alpha-configuration. Conversely, wedge line attachment of a group to the ring system III indicates that the group is attached from above the plane of the paper, and this latter configuration is referred to as the beta-configuration.

The compounds of formulae I and II are conveniently prepared by a series of reactions (see abbreviated reaction sequence I) beginning with oxidation of 2-beta-hydroxymethyl-2-alpha-methyl-(5R)penam-3-alpha-carboxylic acid, the carboxy group of which is protected with a conventional penicillin carboxy protecting group, the identity of which is not critical. The only requirements for the carboxy protecting group are that: (i) it must be stable during oxidation of said starting compound; and (ii) it must be removable from the compound of formula I or formula II using conditions under which the beta-lactam remains substantially intact. Typical examples which can be used are the tetrahydropyranyl group, the benzyl group, substituted benzyl groups (e.g. 4-nitrobenzyl), the benzhydryl group, the 2,2,2-trichloroethyl group, the t-butyl group and the phenacyl group. See further: U.S. Pat. Nos. 3,632,850 and 3,197,466; British Pat. No. 1,041,985, Woodward et al., Journal of the American Chemical Society, 88, 852 (1966); Chauvette, Journal of Organic Chemistry, 36, 1259 (1971); Sheehan et al., Journal of Organic Chemistry, 29, 2006 (1964); and "Cephalosporin and Penicillins, Chemistry and Biology," edited by H. E. Flynn, Academic Press, Inc., 1972. Removal of said carboxy protecting group from compounds of formulae I and II to give corresponding compounds wherein $R_1$ and $R_7$, respectively, are hydrogen is achieved using methods appropriate to the particular protecting group used. Such methods and conditions for their performance are known to those skilled in the art. The preferred protecting groups are benzyl and 4-nitrobenzyl which are readily removed by catalytic hydrogenolysis.

The general procedure for catalytic hydrogenolysis of benzyl or 4-nitrobenzyl protecting groups comprises contacting a solution of the compound to be deprotected with hydrogen, or hydrogen mixed with an inert diluent such as nitrogen or argon, in the presence of a catalytic amount of palladium-on-carbon catalyst. Convenient solvents for this hydrogenolysis are lower-alkanols, such as methanol; ethers such as tetrahydrofuran and dioxane; low molecular weight esters, such as ethyl acetate and butyl acetate; water; and mixtures of these solvents. However, it is usual to choose conditions under which the starting material is soluble. The hydrogenolysis is usually carried out at room temperature and at a pressure from about 0.5 to about 5 kg./cm². The catalyst is usually present in an amount from about 10 percent by weight based on the starting material up to an amount equal in weight to the starting material, although larger amounts can be used. The reaction commonly takes about one hour, after which the compound of formula I wherein $R_1$ is hydrogen or of formula II wherein $R_7$ is hydrogen, is recovered simply by filtration followed by removal of the solvent in vacuo.

The oxidation is carried out by means of a metal permanganate, preferably sodium or potassium permanganate.

The reaction is usually carried out by treating the 2-beta-hydroxymethyl penam reactant with from about 2.0 to about 10 molar equivalents of the permanganate and preferably about 5-6 molar equivalents of the permanganate, in an appropriate solvent system; i.e., one that does not adversely interact with either the starting material or the product. Water is commonly used. If desired, a co-solvent which is miscible with water but will not interact with the permanganate, such as tetrahydrofuran or acetone can be added. The reaction is normally carried out at a temperature in the range from about $-20°$ to about 50° C., and preferably at about ambient temperature. At such a temperature the reaction is normally substantially complete within a period of 40–50 hours. Although the reaction can be carried out under neutral, basic or acidic conditions, it is preferable to operate under acid conditions (pH ~3).

I. Abbreviated Reaction Sequence

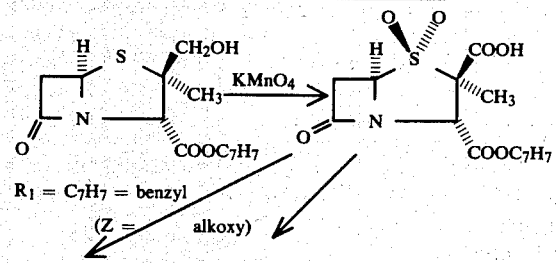

$R_1 = C_7H_7 =$ benzyl
(Z = alkoxy)

-continued
I. Abbreviated Reaction Sequence

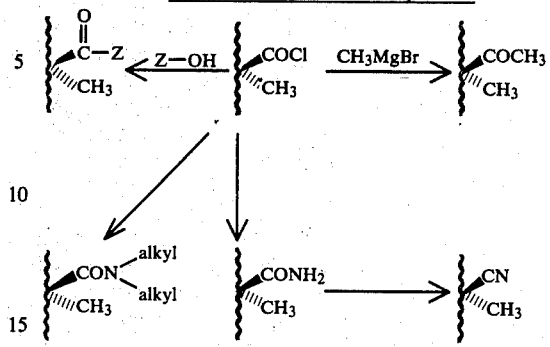

The product is recovered by adding the mixture to water-ethyl acetate followed by cooling and addition of sodium bisulfite at pH 2.5 to reduce excess permanganate and by-product manganese dioxide. The product is recovered by acidifying the mixture to pH 1–2 and extracting said mixture with ethyl acetate. Removal of the solvent affords the product. The thus-produced product is up-graded by dissolution in ethyl acetate-water and adjustment of the pH to 8.5. The aqueous phase is removed, extracted again with ethyl acetate and then acidified and again extracted with ethyl acetate. The product is recovered from this latter extract by evaporation.

The oxidation converts the protected 2-betahydroxymethyl-2-alpha-methyl-(5R)penam-3-alpha-carboxylic acid reactant to the corresponding protected 2-beta-carboxy-2-alpha-methyl-(5R)penam-3-alpha-carboxylic acid 1,1-dioxide compound of formula I wherein $R_2$ is carboxy and $R_1$ is a carboxy protecting group, e.g., benzyl.

The 2-beta-carboxylic acid thus produced is then converted to an acid chloride ($R_2$=COZ=COCl; chlorocarbonyl) by reaction with an appropriate halogenating agent such as oxalyl chloride, thionyl chloride, phosphorous trichloride or phosphorous pentachloride. The reaction is carried out in a reaction-inert solvent such as chloroform, tetrahydrofuran, dioxane or methylene chloride at a low temperature, e.g., from about $-10°$ C. to about $+20°$ C., in the presence of an acid acceptor, such as a tertiary amine. Prior conversion of the carboxylic acid to a metal (e.g., K or Na) salt permits conversion to the acid chloride without the need for an additional acid acceptor. Typical of the tertiary amines which can be used are trialkyl amines such as diisopropylethylamine and triethylamine; N-methylmorpholine, pyridine and N-ethylpiperidine. The reaction is generally heated to about 30°–60° C. for a period of up to about one hour following the initial reaction with the halogenating agent to ensure completion of the reaction.

The acid chloride thus produced can be isolated if desired by evaporation of the solvent and extraction of the acid chloride from the residue. However, it is not necessary to recover the acid chloride from the reaction mixture since the crude acid chloride; i.e., the acid chloride-containing reaction mixture, can be used as is.

The acid chloride serves as convenient starting material for preparing compounds of formula I wherein $R_2$ is defined as CO-Z and Z is an ester or amide moiety. Esters are produced by reaction of the acid chloride with the appropriate alcohol (HOZ) in a reaction-inert solvent, such as those enumerated above, and in the presence of an equivalent amount of an acid acceptor such as the tertiary amine bases enumerated above, at a temperature of from about −10° C. to about 25° C. The esters are recovered by partitioning the reaction product, with or without evaporation of the reaction-inert solvent, between ethyl acetate and water (pH 3–8). The esters are extracted into the ethyl acetate phase and isolated therefrom by standard procedures; e.g., washing with water, drying and evaporating the solvent.

Alternatively, the esters can be prepared directly from the 2-beta-carboxylic acid. A suitable method comprises reacting the 2-beta-carboxylic acid (formula II, $R_7$=protecting group) as its carboxylic salt, with an appropriate alkylating agent, such as an alkyl iodide (e.g., $CH_3I$) or an alkyl sulfate in the presence of a tertiary amine, representative examples of which are cited above. The reaction is conducted in a reaction-inert solvent, e.g., N,N-dimethylformamide or one of the above-mentioned solvents, at ambient temperature. The product is recovered according to the procedure described above but with the added step of washing the ethyl acetate extract with dilute inorganic base (pH~3–8) prior to washing with water, drying and evaporating the solvent.

Formula I and II compounds wherein the 2-beta-substituent is aminocarbonyl or dialkylaminocarbonyl are also prepared from the acid chloride by reaction thereof with ammonia, generally as ammonium hydroxide, or with the appropriate dialkylamine. The ammonia or dialkylamine are generally used in the proportion of at least two moles per mole of acid chloride. Alternatively, one mole of ammonia or dialkylamine can be used and a mole of tertiary amine, such as those mentioned above, added as acid acceptor.

When ammonium hydroxide is used as the source of ammonia, small scale reactions can be carried out with rapid agitation and without the need of co-solvents to form a single phase reaction mixture. Large scale reactions are better conducted with the use of a co-solvent e.g., tetrahydrofuran; or by use of a solution of ammonia in a reaction-inert solvent such as are mentioned above.

When using a dialkylamine as reactant a reaction-inert solvent is desirably used. Suitable solvents are those previously enumerated. The reaction conditions for amide or tertiary amide formation are the same as those described for ester formation. The products are recovered in the same way, with the added step that the ethyl acetate phase is washed with water (pH~3–8) prior to drying and evaporating the ethyl acetate solvent.

The protected 2-beta-aminocarbonyl compound of formula II ($COZ^1$=$CONH_2$) serves as intermediate for the corresponding 2-beta-cyano derivative. The reaction comprises treating the amide with a suitable agent such as phosphorous pentoxide, phosphorous oxychloride or phosphorous pentachloride in a reaction-inert solvent, representatives of which are enumerated above, at an initial temperature of −10° to +10° C. and in the presence of a tertiary amine base such as pyridine or a trialkylamine. The reaction mixture is allowed to warm to ambient temperature and the product recovered according to the procedure described above for recovery of the ester products of formula I.

The 2-beta-acetyl group (formula I, $R_2$=$COZ$=$COCH_3$) is introduced via the intermediary of the 2-beta-chlorocarbonyl derivative (acid chloride) by the Grignard reaction. The acid chloride and an equivalent amount of a Grignard reagent ($CH_3MgBr$) are reacted in a reaction-inert solvent, e.g., ethers such as tetrahydrofuran and dioxane, at a temperature below −10° C., e.g., from −10° to −70° C., and under a nitrogen atmosphere. Following completion of the reaction, the mixture is quenched by addition of acetic acid, then allowed to warm to ambient temperature, and the product recovered by partitioning the reaction mixture between ethyl acetate-water. The ethyl acetate phase is washed (pH 3–8), dried and evaporated.

The formulae I and II compounds wherein $R_1$ and $R_7$ are respectively conventional penicillin carboxy protecting groups, e.g., benzyl or 4-nitrobenzyl, are deprotected as described above.

Compounds of formulae I and II wherein $R_1$ and $R_7$, respectively, are hydrogen, are converted to esters readily hydrolyzable in vivo by esterification of said compounds, the specific method used depending upon the ester-forming residue chosen.

In the case wherein the readily hydrolyzable ester forming residue is selected from the group consisting of 3-phthalidyl, 4-crotonolactonyl, gamma-butylrolacton-4-yl and groups of the formulae I-(b) (2) and I-(b) (3), wherein $R_3$, $R_4$ and $R_5$ are as defined previously, they can be prepared by alkylation of the appropriate compound of formula I, wherein $R_1$ is hydrogen, or a cationic salt thereof as defined below, with a 3-phthalidyl halide, a 4-crotonolactonyl halide, a gamma-butyrolacton-4-yl halide or a compound of the formula

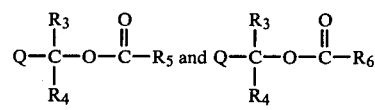

wherein Q is halo, and $R^3$, $R^4$, $R^5$ and $R^6$ are as previously defined. The terms "halide" and "halo" are intended to mean derivatives of chloride, bromine and iodine. The reaction is conveniently carried out by dissolving a salt of said compound of formula I, wherein $R_1$ is hydrogen, in a suitable, polar, organic solvent, such as N,N-dimethylformamide, and then adding about one molar equivalent of the halide. When the reaction has proceeded essentially to completion, the product is isolated by standard techniques. It is often sufficient simply to dilute the reaction medium with an excess of water, and then to extract the product into a water-immiscible organic solvent and then recover same by solvent evaporation. Salts of the starting material which are commonly used are alkali metal salts, such as sodium and potassium salts, and tertiary amine salts, such as triethylamine, ethyldiisopropylamine, N-ethylpiperidine, tetrabutylammonium, N,N-dimethylaniline and N-methylmorpholine salts. The reaction is run at a temperature in the range from about 0° to 100° C., and usually at about 25° C. The length of time needed to reach completion varies according to a variety of factors, such as the concentration of the reactants and the reactivity of the reagents. Thus, when considering the halo compound, the iodide reacts faster than the bromide, which in turn reacts faster than the chloride. In fact, it is sometimes advantageous, when utilizing a chloro compound, to add up to one molar equivalent of an alkali metal iodide. This has the effect of speeding up the reaction. With full regard for the foregoing factors, reaction times of from about 1 to about 24 hours are commonly used.

Alternatively, said esters, especially those bis-esters wherein $R_6$ is an acylaminopenicillanate residue, are prepared by reaction of a halomethyl, e.g., chloromethyl or iodomethyl, ester of a compound of formula I with an alkali metal salt (Na or K) of the appropriate acylaminopenicillin. Further, other esters such as alkylsulfonyloxymethyl and aryl (phenyl, tolyl) sulfonyloxymethyl and 1-chloroethyl esters can be used in place of said halomethyl esters. The reaction conditions used are substantially the same as those described above.

The compounds of formulae I and II, wherein $Z^1$ is hydroxy, and each of $R_1$ and $R_7$ is hydrogen, are acidic and will form salts with basic agents. These salts can be prepared by standard techniques, such as contacting the acidic and basic components, usually in a stoichiometric ratio, in an aqueous, non-aqueous or partially aqueous medium, as appropriate. They are then recovered by filtration, by precipitation with a non-solvent followed by filtration, by evaporation of the solvent, or in the case of aqueous solutions, by lyophilization, as appropriate. Basic agents which are suitably employed in salt formation belong to both the organic and inorganic types, and they include ammonia, organic amines, alkali alkoxides, as well as alkaline earth metal hydroxides, carbonates, hydrides and alkoxides. Representative examples of such bases are primary amines, such as n-propylamine, n-butylamine, aniline, cyclohexylamine, benzylamine and octylamine; secondary amines, such as diethylamine, morpholine, pyrrolidine and piperidine; tertiary amines, such as triethylamine, N-ethylpiperidine, N-methylmorpholine and 1,5-diazabicyclo[4.3.0]-non-5-ene; hydroxides, such as sodium hydroxide, potassium hydroxide, ammonium hydroxide and barium hydroxide; alkoxides, such as sodium ethoxide and potassium ethoxide; hydrides, such as calcium hydride and sodium hydride; carbonates, such as potassium carbonate and sodium carbonate; bicarbonates, such as sodium bicarbonate, and potassium bicarbonate; and alkali metal salts of long-chain fatty acids, such as sodium 2-ethylhexanoate.

The compounds of formula I, wherein $R_1$ is hydrogen are potent inhibitors of microbial beta-lactamases, and will increase the antibacterial effectiveness of beta-lactam antibiotics (penicillins and cephalosporins) against many microorganisms which produce a beta-lactamase, both in vitro and in vivo. The compounds of formula I, wherein $R_1$ is an ester-forming residue readily hydrolyzable in vivo are potent inhibitors of microbial beta-lactamases, and will increase the antibacterial effectiveness of beta-lactam antibiotics (penicillins and cephalosporins) against many microorganisms which produce a beta-lactamase, in vivo. The manner in which compounds of formula I, wherein $R_1$ is hydrogen, increases the effectiveness of a beta-lactam antibiotic in vitro can be appreciated by reference to experiments in which the MIC (Minimum Inhibitory Concentration) of a given antibiotic alone, and a compound of formula I alone, are measured. These MIC's are then compared with the MIC values obtained with a combination of the given antibiotic and a compound of formula I. When the antibacterial potency of the combination is significantly greater than would have been predicted from the potencies of the individual compounds, this is considered to constitute enhancement of activity. The MIC values of combinations are measured using the method described by Barry and Sabath in "Manual of Clinical Microbiology", edited by Lenette, Spaulding and Truant, 2nd edition, 1974, American Society for Microbiology.

The compounds of formula I, and salts thereof, enhance the antibacterial effectiveness of beta-lactam antibiotics in vivo, i.e., they lower the amount of antibiotic which is needed to protect mice against an otherwise lethal inoculum of certain beta-lactamase producing bacteria.

The ability of the compounds of the formula I, and salts thereof, to enhance the effectiveness of a beta-lactam antibiotic against beta-lactamase-producing bacteria makes them valuable for co-administration with beta-lactam antibiotics in the treatment of bacterial infections in humans. In the treatment of a bacterial infection, said compound of formula I can be comingled with the beta-lactam antibiotic, and the two agents thereby administered simultaneously. Alternatively, said compound of the formula I can be administered as a separate agent during a course of treatment with a beta-lactam antibiotic. In some instances it will be advantageous to pre-dose the subject with the compound of the formula I before initiating treatment with a beta-lactam antibiotic.

When using a compound of formula I, or a salt thereof to enhance the effectiveness of a beta-lactam antibiotic in a human subject, it can be administered alone or it can be mixed with pharmaceutically acceptable carriers or diluents. It can be administered orally or parenterally, i.e., intramuscularly, subcutaneously or intraperitoneally. The carrier or diluent is chosen on the basis of the intended mode of administration. For example, when considering the oral mode of administration, a compound of this invention of formula I can be used in the form of tablets, capsules, lozenges, troches, powders, syrups, elixirs, aqueous solutions and suspensions, and the like, in accordance with standard pharmaceutical practice. In the case of tablets for oral use, carriers which are commonly used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols, e.g., polyethylene glycols having molecular weights from 2,000 to 4,000. When aqueous suspensions are required for oral use, the active ingredient is combined with emulsifying and suspending agents. If desired, certain sweetening and/or flavoring agents can be added. For parenteral administration, which includes intramuscular, intraperitoneal, subcutaneous and intravenous use, sterile solutions of the active ingredient are usually prepared, and the pH of the solutions are suitably adjusted and buffered. For intravenous use, the total concentration of solutes should be controlled to render the preparation isotonic. A pharmaceutical composition containing a compound of this invention will normally contain from about 20 to about 95 percent by weight of the compound of formula I.

When using a compound of formula I in combination with another beta-lactam antibiotic, the compound can be administered orally or parenterally, i.e., intramuscularly, subcutaneously or intraperitoneally. Although the prescribing physician will ultimately decide the dosage to be used in a human subject, the ratio of the daily dosages of the penam of this invention and the beta-lactam antibiotic will normally be in the range from about 1:3 to 3:1. Additionally, when using a compound of this invention in combination with another beta-lactam antibiotic, the daily oral dosage of each component will normally be in the range from about 10 to about 200 mg.

per kilogram of body weight and the daily parenteral dosage of each component will normally be about 10 to about 400 mg. per kilogram of body weight. These figures are illustrative only, however, and in some cases it may be necessary to use dosages outside these limits.

Typical beta-lactam antibiotics with which a compound of formula I or salts or esters readily hydrolyzable in vivo can be co-administered are penicillins and cephalosporins which are used commercially. Representative of such compounds are:

6-(2-phenylacetamido)penicillanic acid,
6-(D-2-amino-2-phenylacetamido)penicillanic acid,
6-(D-2-amino-2-[4-hydroxyphenyl]acetamido)penicillanic acid,
6-(2-carboxy-2-phenylacetamido)penicillanic acid,
6-(2-carboxy-2-[3-thienyl]acetamido)penicillanic acid,
6-(D-2-[4-ethylpiperazin-2,3-dione-1-carboxamido]-2-phenylacetamido)penicillanic acid,
acetoxymethyl 6-(D-2-amino-2-phenylacetamido)-penicillanate,
pivaloyloxymethyl 6-(2-phenylacetamido)penicillanate,
pivaloyloxymethyl 6-(D-2-amino-2-[4-hydroxyphenyl]acetamido)penicillanate,
1-(ethoxycarbonyloxy)ethyl 6-(D-2-amino-2-[4-hydroxyphenyl]-acetamido)penicillanate,
3-phthalidyl 6-(2-phenylacetamido)penicillanate,
3-phthalidyl 6-(D-2-amino-2-phenylacetamido)penicillanate,
7-(D-2-amino-2-[4-hydroxyphenyl]acetamido)-desacetoxycephalosporanic acid,
7-(2-[2-amino-4-thiazolyl]-2-[methoxyimino]acetamido)cephalosporanic acid,
7-(D-2-amino-2-phenylacetamido)desacetoxycephalosporanic acid,
7-alpha-methoxy-7-(2-[2-thienyl]acetamido)-3-carbamoyloxymethyl-3-desacetoxymethylcephalosporanic acid,
7-(D-2-amino-2-phenylacetamido)cephalosporanic acid,
7-(D-2-[4-ethylpiperazin-2,3-dione-1-carboxamido]-2-[4-hydroxyphenyl]acetamido)-3-[1-methyl-5-tetrazolyl]thiomethyl)-3-desacetoxymethylcephalosporanic acid, and the pharmaceutically-acceptable salts thereof.

As will be appreciated by one skilled in the art, some of the above beta-lactam compounds are effective when administered orally or parenterally, while others are effective only when administered by the parenteral route. When a compound of formula I, or a salt or an ester thereof readily hydrolyzable in vivo, is to be used simultaneously (i.e., co-mingled) with a beta-lactam antibiotic which is effective only on parenteral administration, a combination formulation suitable for parenteral use will be required. When the compound of formula I or salt or ester thereof is to be used simultaneously (co-mingled) with a beta-lactam antibiotic which is effective orally or parenterally, combinations suitable for either oral or parenteral administration can be prepared. Additionally, it is possible to administer preparation of the compound of formula I or salt or ester thereof orally while at the same time administering a further beta-lactam antibiotic parenterally; and it is also possible to administer preparations of the compound of formula I or salt or ester thereof parenterally, while at the same time administering the further beta-lactam antibiotic orally.

The following examples are provided solely for the purpose of further illustration. In the examples presented, no effort was made to optimize the reaction conditions or to recover the maximum amount of product from a given reaction. Infrared (IR) spectra were measured as potassium bromide discs (KBr discs), and diagnostic absorption bands are reported in wave numbers ($cm^{-1}$). Nuclear magnetic resonance spectra (NMR) were measured at 60 MHz for solutions in deuterochloroform ($CDCl_3$) or perdeutero dimethyl sulfoxide (DMSO-$d_6$), and peak positions are expressed in parts per million (ppm) downfield) from tetramethylsilane. The following abbreviations for peak shapes are used: s, singlet; d, doublet; q, quartet; m, multiplet.

EXAMPLE 1

Benzyl 2-beta-Carboxy-2-alpha-Methyl-(5R)-Penam-3-alpha-Carboxylate 1,1-Dioxide

Powdered potassium permanganate (17.96 g.) was added portionwise to a solution of benzyl 2-beta-hydroxymethyl-2-alpha-methyl-(5R)penam-3-alpha-carboxylate (5.82 g.) in acetone (300 ml.)-water (60 ml.) cooled to 0°–5° C. in an ice-bath. After addition of each portion of permanganate, the apparent pH of the mixture was adjusted to 3.0 by addition of 25% phosphoric acid. The mixture was stirred for one-half hour at 0°–5° C. following completion of permanganate addition and the cooling bath removed. Periodic adjustments of pH were made as needed to maintain apparent pH 3.0.

The mixture was stirred for an additional 50 hours then added to water (800 ml.)-ethyl acetate (300 ml.). The resulting mixture was cooled to 15° C. and 10% sodium bisulfite solution added at pH 2.5 until the brown precipitate of manganese dioxide dissolved. The pH was then adjusted to 1.6 by means of 2 N HCl. The ethyl acetate phase was removed and the aqueous phase extracted with additional ethyl acetate (300 ml.). The ethyl acetate phases were combined, washed with brine (2×100 ml.) and dried ($Na_2SO_4$). Evaporation under reduced pressure (aspirator) gave a gummy solid.

The gummy solid was taken up in ethyl acetate (50 ml.)-water (25 ml.) and the pH adjusted to 8.5 by means of 5% aqueous NaOH. The phases were separated and the aqueous phase extracted once again with ethyl acetate (25 ml.). The aqueous phase was adjusted to pH 1.6 by means of 2 N HCl and then extracted with ethyl acetate (50 ml.). The ethyl acetate extract was washed with brine (2×20 ml.), dried ($Na_2SO_4$) and evaporated in vacuo to give 2.1 g. of the title product as a solid.

Recrystallization from ethyl acetate/ether afforded an analytical sample: m.p. 122°–124° (dec.)

Anal. Calcd. for $C_{15}H_{15}NO_7S$: 50.98%C; 4.28%H; 3.96%N. Found: 50.82%C; 4.35%H; 3.99%N.

NMR ($CDCl_3$ +DMSO-$d_6$) δ 1.58 (3H, s), 3.48 (2H, m), 4.84 (1H, dd J=2, 4 Hz), 5.22 (2H, s), 5.46 (1H, s), 7.33 (5H, s).

In like manner, the 2-beta-hydroxymethyl-2-alpha-methyl-(5R)penam-3-alpha-carboxylic acid esters of Preparation C are converted to the corresponding 2-beta-carboxy-2-alpha-methyl-(5R)penam-3-alpha-carboxylic acid 1,1-dioxide esters wherein the ester group ($R_1$) is as defined in Preparation F.

EXAMPLE 2

Benzyl 2-beta-Chlorocarbonyl-2-alpha-Methyl-(5R)-Penam-3-alpha-Carboxylate 1,1-Dioxide Oxalyl chloride (0.37 ml.) was added with stirring to a solution of benzyl 2-beta-carboxy-2-alpha-methyl-(5R)penam-3-alpha-carboxylate 1,1-dioxide (1.25 g.) in chloroform (12 ml.) at 0° C. under a nitrogen atmosphere. Diisopropyl ethyl amine (0.68 ml.) was added immediately in a single portion. The resulting brown, foaming mixture was then warmed to 50° C. on a water bath and stirred for 30 minutes. The crude acid chloride thus formed was used without further purification.

NMR (CDCl$_3$) δ 1.70 (3H, s), 3.57 (2H, m), 4.78 (1H, dd, J=2, 4 Hz), 5.23 (2H, ABq, J=12) 5.47 (1H, s), 7.34 (5H, s).

The remaining esters of Example 1 are similarly converted to their corresponding 2-beta-chlorocarbonyl derivatives wherein the ester group ($R_1$) is as defined in Preparation F.

EXAMPLE 3

Benzyl 2-beta-Carbomethoxy-2-alpha-Methyl-(5R)-Penam-3-alpha-Carboxylate 1,1-Dioxide

Method A

Diisopropyl ethyl amine (0.117 ml.) was added to a solution of benzyl 2-beta-carboxy-2-alpha-methyl-(5R)penam-3-alpha-carboxylate 1,1-dioxide (24 mg.) and methyl iodide (0.3 ml.) in N,N-dimethylformamide (1 ml.) at room temperature and the mixture stirred for 90 minutes. Ethyl acetate (15 ml.) and water (30 ml.) were added to the mixture and the pH then adjusted to 3.0 by addition of 2 N HCl. The ethyl acetate layer was removed and washed with water (2×25 ml.) at pH 8.5, followed by brine (20 ml.), and then dried (Na$_2$SO$_4$). The ethyl acetate was evaporated in vacuo to give the product as an oil. The oil was taken up in chloroform (10 ml.) and the chloroform removed by evaporation in vacuo. The process was repeated once again to assure removal of all ethyl acetate. The oily residue crystallized upon standing (20 mg.).

It was purified by thin-layer chromatography on silica gel using 2:1 hexane-ethyl acetate as eluant.

Rf=0.25

NMR (CDCl$_3$) δ 1.52 (3H, s), 3.50 (2H, m), 3.86 (3H, s), 4.63 (1H, m), 5.22 (2H, s), 5.54 (1H, s), 7.37 (5H, s).

Substitution of an equimolar amount of ethyl iodide, n-propyl iodide or n-butyl iodide for methyl iodide in the above procedure, but using reaction times of 24-48 hours, affords the corresponding ethyl, n-propyl and n-butyl esters.

Method B

Pyridine (10 drops) and methanol (8 drops) were added to 0.1 mmole of benzyl 2-beta-chlorocarbonyl-2-alpha-methyl-(5R)penam-3-alpha-carboxylate 1,1-dioxide (product of Example 2) under a nitrogen atmosphere cooled in an ice bath and the mixture stirred for 90 minutes. It was then partitioned between ethyl acetate (20 ml.) and water (20 ml.) and the pH adjusted to 3.0. The ethyl acetate layer was separated, washed with water (10 ml.) at pH 3.0, followed by brine (20 ml.) and then dried (Na$_2$SO$_4$). Removal of ethyl acetate in vacuo gave 35 mg. of the title product.

Its NMR spectrum was identical to that of the product of Method A.

Repetition of the above procedure but replacing methanol with an equimolar amount of n-propanol, isopropanol or n-butanol affords the corresponding n-propyl, isopropyl and n-butyl esters.

Repetition of the above procedure of Method B but using the appropriate ester of 2-beta-chlorocarbonyl-2-alpha-methyl-(5R)penam-3-alpha-carboxylic acid 1,1-dioxide and the appropriate alcohol in place of the reactants of Method B affords compounds having the formula

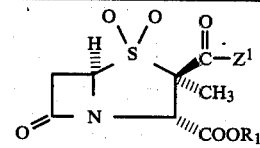

| Z | $R_1$ |
|---|---|
| methoxy | p-nitrobenzyl |
| n-butoxy | p-nitrobenzyl |
| methoxy | pivaloyloxymethyl |
| n-propoxy | pivaloyloxymethyl |
| ethoxy | 3-phthalidyl |
| methoxy | 4-crotonolactonyl |
| isopropoxy | γ-butyrolacton-4-yl |
| methoxy | acetoxymethyl |
| n-butoxy | acetoxymethyl |
| ethoxy | 1-acetoxyethyl |
| ethoxy | 1-methyl-1-(acetoxy)ethyl |
| methoxy | hexanoyloxymethyl |
| methoxy | 1-methyl-1-(hexanoyloxy)ethyl |
| methoxy | methoxycarbonyloxymethyl |
| isopropoxy | methoxycarbonyloxymethyl |
| methoxy | propoxycarbonyloxymethyl |
| n-butoxy | 1-(ethoxycarbonyloxy)ethyl |
| ethoxy | 1-methyl-1-(ethoxycarbonyloxy)ethyl |
| methoxy | 1-methyl-1-(hexanoyloxycarbonyloxy)methyl |
| ethoxy | 1-(ethoxycarbonyloxy)methyl |

EXAMPLE 4

2-beta-Carbomethoxy-2-alpha-Methyl-(5R)Penam-3-alpha-Carboxylic Acid 1,1-Dioxide A solution of benzyl 2-beta-carbomethoxy-2-alpha-methyl-(5R)penam-3-alpha-carboxylate 1,1-dioxide (44 mg.) in methanol (20 ml.)-water (5 ml.) was hydrogenolyzed in a Paar apparatus over 10% Pd/C (200 mg.) at 3.52 kg./cm$^2$ of H$_2$ (50 psi) for 20 minutes at room temperature. The catalyst was removed by filtration and washed with methanol/water. The filtrate was evaporated in vacuo to remove the methanol and the aqueous residue extracted with ethyl acetate at pH 1.6 (2×20 ml.). The combined ethyl acetate extracts were dried (Na$_2$SO$_4$) and evaporated in vacuo to give a glass-like residue. The product was crystallized slowly from deuterochloroform.

NMR (CDCl$_3$) δ 1.75 (3H, s), 3.53 (2H, m), 3.90 (3H, s), 4.68 (1H, m), 5.49 (1H, s).

The remaining benzyl and p-nitrobenzyl esters of Example 3 are debenzylated in like manner to the corresponding 2-beta-carboalkoxy-2-alpha-methyl-(5R)-penam-3-alpha-carboxylic acid 1,1-dioxides.

EXAMPLE 5

Benzyl 2-beta-Carbethoxy-2-alpha-Methyl-(5R)Penam-3-alpha-Carboxylate 1,1-Dioxide Pyridine (0.091 ml.) and ethanol (0.065 ml.) were added to 0.283 mmole of benzyl 2-beta-chlorocarbonyl-2-alpha-methyl-(5R)penam-3-alpha-carboxylate 1,1-dioxide (prepared according to the method of Example 2 but using $CH_2Cl_2$ as solvent in place of chloroform) in methylene chloride (3 ml.) under a nitrogen atmosphere at 0° C. and the mixture stirred for a half hour. It was then warmed to room temperature and the methylene chloride removed in vacuo. The residue was partitioned between ethyl acetate (15 ml.)-water (15 ml.) at pH 3.0. The ethyl acetate phase was separated and washed successively with water (15 ml.) at pH 3.0, water (10 ml.) no pH adjustment, water (15 ml.) at pH 8.5, brine (15 ml.) and dried ($Na_2SO_4$). Evaporation of the ethyl acetate in vacuo gave 106 mg. of product as an oil.

NMR ($CDCl_3$) δ 1.26 (3H, t, J=7 Hz), 1.54 (3H, s), 3.49 (2H, m), 4.31 (2H, q, J=7), 4.58 (1H, m), 5.17 (2H, Abq), 5.48 (1H, s), 7.30 (5H, s).

EXAMPLE 6

2-beta-Carbethoxy-2-alpha-Methyl-(5R)Penam-3-alpha-Carboxylic Acid 1,1-Dioxide

A mixture of benzyl 2-beta-carbethoxy-2-alpha-methyl-(5R)penam-3-alpha-carboxylate 1,1-dioxide (160 mg.), tetrahydrofuran (25 ml.)-water (10 ml.) and 5% Pd/$CaCO_3$ (300 mg.) was hydrogenolyzed in a Paar apparatus at 3.37 kg./$cm^2$. of $H_2$ (48 psi) for 15 minutes at room temperature. The catalyst was then removed by filtration and washed with tetrahydrofuran (15 ml.)-water (6 ml.). The filtrate was evaporated in vacuo to remove the tetrahydrofuran. Ether (20 ml.) was added to the aqueous residue (pH 7.8), the mixture thoroughly mixed and the phases separated. The aqueous phase was acidified to pH 1.6 (2 N HCl) and extracted with ethyl acetate (30 ml.). The extract was dried ($Na_2SO_4$) and evaporated in vacuo to a clear, amorphous residue. The residue was taken up in ethyl acetate (5 ml.) and evaporated in vacuo. This step was repeated once again. To remove traces of ethyl acetate, chloroform (5 ml.) was added to the residue and then removed by evaporation in vacuo. The addition and removal of chloroform was repeated once again to give 100 mg. of the title product as a clear, amorphous mass (a glass).

NMR ($CDCl_3$) δ 1.33 (3H, t, J=7 Hz), 1.74 (3H, s), 3.50 (2H, m), 4.34 (2H, q, J=7 Hz), 4.65 (1H, s), 5.48 (1H, s).

EXAMPLE 7

Benzyl 2-beta-(2-Acetamidoethoxycarbonyl)-2-alpha-Methyl-(5R)Penam-3-alpha-Carboxylate 1,1-Dioxide To a 0° C. solution of benzyl 2-beta-chlorocarbonyl-2-alpha-methyl-(5R)penam-3-alpha-carboxylate 1,1-dioxide (0.95 mmole) in chloroform (product of Example 2) under nitrogen in a cooling bath at 0° C. was added a solution of 2-acetamidoethanol (309 mg.) and diisopropylethylamine (0.348 ml.) in methylene chloride (2 ml.) with rapid stirring. After five minutes of rapid stirring at 0° C., the cooling bath was removed and the mixture stirred for an additional 90 minutes. The mixture was evaporated in vacuo and the residue partitioned between ethyl acetate (30 ml.)-water (30 ml.). The phases were separated and the ethyl acetate phase washed successively with dilute (pH 2.5) aqueous HCl (20 ml.), water (10 ml.), dilute aqueous (pH 8.0) NaOH (20 ml.), water (10 ml.), and brine (20 ml.) and then dried ($Na_2SO_4$). The dried extract was evaporated in vacuo, chloroform (5 ml.) added to the residue and the chloroform removed in vacuo. This step was repeated two more times to give 213 mg. of product as a dark oil.

It was purified by column chromatography on silica gel using ethyl acetate as eluant. The column was monitored by thin-layer chromatography and appropriate fractions combined and evaporated to give 73 mg. of product as an oil.

NMR ($CDCl_3$) δ 1.53 (3H, s), 1.94 (3H, s), 3.51 (4H, m), 4.31 (2H, m), 4.65 (1H, m), 5.19 (2H, s), 5.50 (1H, s), 6.2 (1H, broad s), 7.30 (5H, s).

By means of this procedure, the 2-beta-chlorocarbonyl-2-alpha-methyl-(5R)penam-3-alpha-carboxylic acid 1,1-dioxide esters of Example 2 are converted to the corresponding esters of 2-beta-(2-acetamidoethoxycarbonyl)-2-alpha-methyl-(5R)penam-3-alpha-carboxylic acid 1,1-dioxide.

EXAMPLE 8

2-beta-(2-Acetamidoethoxycarbonyl)-2-alpha-Methyl-(5R)Penam-3-alpha-Carboxylic Acid 1,1-Dioxide Benzyl 2-beta-(2-acetamidoethoxycarbonyl)-2-alpha-methyl-(5R)penam-3-alpha-carboxylate 1,1-dioxide (73 mg.) in tetrahydrofuran (20 ml.)-water (5 ml.) was hydrogenolyzed in a Paar apparatus at room temperature over 10% Pd/C (150 mg.) at 3.52 kg/$cm^2$ of $H_2$ (50 psi) for 20 minutes. The catalyst was then removed by filtration, washed with tetrahydrofuran (20 ml.)-water (10 ml.) and the combined filtrate plus washing evaporated in vacuo to remove most of the tetrahydrofuran, leaving an aqueous solution. Ethyl acetate (20 ml.) was added to the aqueous residue and the pH adjusted to 8.0. The phases were mixed and then separated. Fresh ethyl acetate (20 ml.) was added to the aqueous phase and the pH adjusted to 1.6. After thorough mixing, the ethyl acetate phase was separated, washed with brine (10 ml.) amd dried ($Na_2SO_4$). The ethyl acetate was evaporated in vacuo and chloroform (5 ml.) added to the residue. Evaporation of the chloroform in vacuo gave 15 mg. of the title product as a glass which crystallized on standing.

NMR (Acetone-$d_6$) δ 1.74 (3H, s), 1.90 (3H, s), 3.58 (4H, m), 4.32 (2H, t, J=5.6 Hz), 4.68 (2H, broad), 4.97 (1H, dd, J=2,4), 5.47 (1H, s).

Following the procedure of Example 7 and that of the present example but substituting 3-acetamidopropanol or 4-acetamidobutanol for 2-acetamidoethanol, affords the corresponding compounds wherein the 2-beta-substituent is 3-acetamidopropoxycarbonyl or 4-acetamidobutoxycarbonyl.

EXAMPLE 9

Benzyl 2-beta-(2-Hydroxyethoxycarbonyl)-2-alpha-Methyl-(5R)Penam-3-alpha-Carboxylate 1,1-Dioxide A solution of benzyl 2-beta-chlorocarbonyl-2-alpha-methyl-(5R)penam-3-alpha-carboxylate 1,1-dioxide (0.53 mmole) in chloroform (2.5 ml.) was added with good stirring to a solution of ethylene glycol (1.1 ml.) and pyridine (0.3 ml.) in methylene chloride (3 ml.) at 0° C. under a nitrogen atmosphere. The mixture was stirred for one hour at 0° C. then allowed to come to room temperature. Ethyl acetate (20 ml.) and water (10 ml.) were added to the mixture, the pH adjusted to 2.5 by addition of 2 N phosphoric acid and the mixture thoroughly mixed. The phases were separated and the ethyl acetate phase again washed with water (10 ml.) at pH 2.5. It was then separated, washed with water (4×10 ml.), brine (15 ml.) and dried ($Na_2SO_4$). Evaporation in vacuo gave 0.192 g. of the title product as an oil.

NMR ($CDCl_3$) δ 1.53 (3H, s), 2.94 (1H, broad s), 3.50 (2H, m), 3.76 (2H, m), 4.33 (2H, m), 4.66 (1H, m), 5.21 (2H, s), 5.52 (1H, s), 7.35 (5H, s).

EXAMPLE 10

2-beta-(2-Hydroxyethoxycarbonyl)-2-alpha-Methyl-(5R)Penam-3-alpha-Carboxylic Acid 1,1-Dioxide Benzyl 2-beta-(2-hydroxyethoxycarbonyl)-2-alpha-methyl-(5R)penam-3-alpha-carboxylate 1,1-dioxide (192 mg.) was hydrogenolyzed in tetrahydrofuran (30 ml.)-water (5 ml.) over 10% Pd/C (300 mg.) at 3.37 kg/cm$^2$ of $H_2$ (48 psi) and room temperature in a Paar apparatus for 20 minutes. The catalyst was removed by filtration, washed with ethyl acetate (30 ml.)-water (10 ml.) and the combined filtrate and wash solution chilled in an ice bath. The pH was adjusted to 1.6, the phases mixed and then separated. The aqueous phase was extracted with ethyl acetate (30 ml.), and the combined ethyl acetate extracts washed with brine (20 ml.) and then dried ($Na_2SO_4$). Evaporation in vacuo gave the title product (120 mg.) as a glass.

NMR (Acetone-$d_6$) δ 1.79 (3H, s), 3.36 (1H, dd, J=2, 17 Hz), 3.77 (1H, dd, J=4, 17 Hz), 3.80 (2H, t, J=5), 4.35 (2H, t, J=5), 4.98 (1H, dd, J=2,4 Hz), 5.46 (1H, s), 6.93 (2H, broad).

Following the procedure of Example 9 but substituting an equimolar amount of propylene glycol, trimethylene glycol or 1,4-butylene glycol for ethylene glycol affords the corresponding omega-hydroxyalkoxycarbonyl derivatives, which are hydrogenolyzed by the procedure of this example.

EXAMPLE 11

Benzyl 2-beta-(2-Carbomethoxymethoxycarbonyl)-2-alpha-Methyl-(5R)Penam-3-alpha-Carboxylate 1,1-Dioxide A solution of pyridine (0.3 ml.) and methyl glycolate (0.391 ml.) in methylene chloride (1 ml.) was added to a solution of benzyl 2-beta-chlorocarbonyl-2-alpha-methyl-(5R)penam-3-alpha-carboxylate 1,1-dioxide (0.53 mmols) in deuterochloroform (product of Example 2) at 0° C. under a nitrogen atmosphere. The mixture was stirred at 0° C. for one hour and then at room temperature for one hour. The reaction mixture was worked up according to the procedure of Example 9 to give 256 mg. of the title product as an oil.

NMR ($CDCl_3$) δ 1.63 (3H, s), 3.49 (2H, m), 3.73 (3H, s), 4.70 (3H, m), 5.21 (2H, s), 5.53 (1H, s), 7.32 (5H, s).

Repetition of this procedure but using equimolar amounts of ethyl glycolate, propyl glycolate or butyl glcolate in place of methyl glycolate affords the corresponding carboalkoxymethoxycarbonyl compounds.

EXAMPLE 12

2-beta-(2-Carbomethoxymethoxycarbonyl)-2-alpha-Methyl-(5R)Penam-3-alpha-Carboxylic Acid 1,1-Dioxide Following the procedure of Example 10, but using acetone-water (5:1) rather than tetrahydrofuran-water as solvent and 400 mg. of 10% Pd/C, benzyl 2-beta-(2-carbomethoxymethoxycarbonyl)-2-alpha-methyl-(5R)penam-3-alpha-carboxylate 1,1-dioxide (256 mg.) was converted to the title product (130 mg.).

NMR ($CDCl_3$) δ 1.82 (3H, s), 3.55 (2H, m), 3.80 (3H, s), 4.84 (3H, m), 5.50 (1H, s).

Similarly, the remaining benzyl and p-nitrobenzyl esters of Example 11 are hydrogenolyzed to the corresponding acids.

EXAMPLE 13

Benzyl 2-beta-Acetyl-2-alpha-Methyl-(5R)Penam-3-alpha-carboxylate 1,1-Dioxide

A solution of benzyl 2-beta-chlorocarbonyl-2-alpha-methyl-(5R)penam-3-alpha-carboxylate 1,1-dioxide (1.0 mmole, prepared according to Example 2, followed by evaporation of the chloroform and replacement by tetrahydrofuran) in tetrahydrofuran (5 ml.) and under a nitrogen atmosphere was cooled to −70° C. An ether solution of methyl magnesium bromide (0.956 ml. of 2.3 M) was then added dropwise with rapid stirring, and stirring at −70° C. continued for 25 minutes following completion of addition. Acetic acid (0.3 ml.) in tetrahydrofuran (2 ml.) was added, the cooling bath removed, and the mixture allowed to come to room temperature. It was then distributed between ethyl acetate (30 ml.)-water (20 ml.), the ethyl acetate phase removed and washed successively with aqueous acid (10 ml.) at pH 2.5, at pH 6.5 (10 ml.), water (10 ml.), brine (10 ml.), and then dried ($Na_2SO_4$). Evaporation in vacuo gave 130 mg. of the title compound.

This procedure was repeated once again and the combined products chromatographed on a silica gel column using ethyl acetate as eluant.

Appropriate fractions were combined and evaporated in vacuo to give 76 mg. of the pure product.

NMR ($CDCl_3$) δ 1.61 (3H, s), 2.43 (3H, s), 3.51 (2H, m), 4.66 (1H, m), 5.22 (2H, s), 5.64 (1H, s), 7.37 (5H, s).

Substitution of the 2-beta-chlorocarbonyl-2-alpha-methyl-(5R)penam-3-alpha-carboxylic acid 1,1-dioxide esters of Preparation F in the above procedure affords the corresponding 2-beta-acetyl-2-alpha-methyl-(5R)penam-3-alpha-carboxylic acid 1,1-dioxide esters.

EXAMPLE 14

2-beta-Acetyl-2-alpha-Methyl-(5R)Penam-3-alpha-Carboxylic Acid 1,1-Dioxide

Benzyl 2-beta-acetyl-2-alpha-methyl-(5R)penam-3-alpha-carboxylate 1,1-dioxide (76 mg.) was hydrogenolyzed over 150 mg. of 10% Pd/C according to the procedure of Example 10 to give the title product as an oil. Chloroform (5 ml.) was added to the oil and subsequently removed in vacuo to remove ethyl acetate. This treatment was repeated.

The oily residue was triturated with carbon tetrachloride (5 ml.) and the carbon tetrachloride phase (containing butylated hydroxytoluene stabilizer from the tetrahydrofuran) was removed by decantation. This treatment was repeated two times. The carbon tetrachloride insoluble portion was combined with 10 ml. acetone. Insolubles were removed by filtration and acetone was removed from the filtrate by evaporation at reduced pressure leaving 40 mg. of product as an oil.

NMR (Acetone-$d_6$) δ 1.76 (3H, s), 2.37 (3H, s), 3.23 (1H, dd, J=2,16 Hz), 3.70 (1H, dd, J=4, 16 Hz), 4.97 (1H, dd, J=2,4), 5.42 (1H, s).

EXAMPLE 15

Benzyl 2-beta-Dimethylaminocarbonyl-2-alpha-Methyl-(5R)Penam-3-alpha-Carboxylate 1,1-Dioxide Aqueous dimethylamine (0.277 ml. of 25% solution) was added to benzyl 2-beta-chlorocarbonyl-2-alpha-methyl-(5R)penam-3-alpha-carboxylate 1,1-dioxide (0.708 mmole) in chloroform (prepared according to Example 2) under a nitrogen atmosphere at 0° C. with rapid stirring. The mixture was stirred for one hour and then added to a mixture of ethyl acetate (25 ml.)-water (15 ml.). The pH was adjusted to 3.0 by addition of 2 N $H_3PO_4$, the mixture thoroughly mixed, and the phases separated. The ethyl acetate phased was washed with water (2×15 ml.), then extracted at pH 8.5 with aqueous NaOH (20 ml.), followed by brine (20 ml.) and dried ($Na_2SO_4$). Evaporation of the ethyl acetate extract in vacuo gave 215 mg. of the title product which was purified by chromatography on silica gel using 10% ethyl acetate/methylene chloride as eluting solvent. Yield=131 mg. as an oil.

NMR (CDCl$_3$) δ 1.68 (3H, s), 3.11 (6H, s), 3.48 (2H, m), 4.70 (1H, m), 5.11 (2H, s), 6.34 (1H, s), 7.35 (5H, s).

In like manner the following compounds are prepared from the appropriate reactants; i.e., dialkylamine and ester of 2-beta-chlorocarbonyl-2-alpha-methyl-(5R)penam-3-alpha-carboxylic acid 1,1-dioxide:

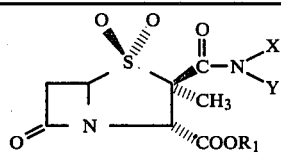

| X | Y | R$_1$ |
|---|---|---|
| n-C$_4$H$_9$ | CH$_3$ | benzyl |
| n-C$_4$H$_9$ | n-C$_4$H$_9$ | benzyl |
| CH$_3$ | CH$_3$ | p-nitrobenzyl |
| CH$_3$ | CH$_3$ | 3-phthalidyl |
| C$_2$H$_5$ | C$_2$H$_5$ | 3-phthalidyl |
| i-C$_3$H$_7$ | i-C$_3$H$_7$ | 4-crotonolactonyl |
| CH$_3$ | CH$_3$ | γ-butyrolacton-4-yl |
| CH$_3$ | CH$_3$ | acetoxymethyl |
| CH$_3$ | n-C$_3$H$_7$ | acetoxymethyl |
| n-C$_4$H$_9$ | n-C$_4$H$_9$ | acetoxymethyl |
| CH$_3$ | CH$_3$ | 1-acetoxyethyl |
| C$_2$H$_5$ | C$_2$H$_5$ | hexanoyloxymethyl |
| CH$_3$ | CH$_3$ | methoxycarbonyloxymethyl |
| CH$_3$ | CH$_3$ | 1-(ethoxycarbonyloxy)-ethyl |
| CH$_3$ | i-C$_3$H$_7$ | propoxycarbonyloxymethyl |

EXAMPLE 16

2-beta-Dimethylaminocarbonyl-2-alpha-Methyl-(5R)Penam-3-alpha-Carboxylic Acid 1,1-Dioxide Benzyl 2-beta-dimethylaminocarbonyl-2-alpha-methyl-(5R)penam-3-alpha-carboxylate 1,1-dioxide (131 mg.) in tetrahydrofuran (20 ml.)-water (10 ml.) was hydrogenolyzed in a Paar apparatus over 5% Pd/CaCO$_3$ (400 mg.) at 3.52 kg/cm$^2$ (50 psi) of H$_2$ for 20 minutes at room temperature. The catalyst was then removed by filtration and washed with tetrahydrofuran (20 ml.)-water (20 ml.). The tetrahydrofuran was evaporated under reduced pressure from the combined filtrate plus wash solution. The aqueous solution (pH 5.0) was extracted with ether (30 ml.) and then freeze-dried to give 85 mg. of the calcium salt of the title product.

NMR (D$_2$O) δ 1.99 (3H, s), 3.23 (6H, s), 3.60 (2H, m), 5.12 (1H, dd, J=2,4 Hz), 5.73 (1H, s).

In like manner, the benzyl and p-nitrobenzyl esters of Example 15 are debenzylated to the corresponding acids.

EXAMPLE 17

Benzyl 2-beta-Aminocarbonyl-2-alpha-Methyl-(5R)Penam-3-alpha-Carboxylate 1,1-Dioxide Aqueous ammonium hydroxide (2.832 mmoles) was added in one portion to a rapidly stirring chloroform solution of benzyl 2-beta-chlorocarbonyl-2-alpha-methyl-(5R)penam-3-alpha-carboxylate 1,1-dioxide (1.416 mmoles prepared according to Example 2) under a nitrogen atmosphere at 0° C. The mixture was stirred for one hour at 0° C. and then added to ethyl acetate (30 ml.)water (30 ml.). The pH was adjusted to 3.0, the mixture thoroughly mixed, and the phases then separated. The ethyl acetate phase was washed successively with water (2×20 ml.), dilute aqueous base (pH 8.0, 20 ml.), brine (20 ml.) and then dried over Na$_2$SO$_4$. Evaporation of the ethyl acetate in vacuo gave 312 mg. of crude product which was chromatographed on silica gel using 25% ethyl acetate-methylene chloride. Evaporation of appropriate fractions gave 190 mg. of the title product as an oil.

NMR (CDCl$_3$) δ 1.59 (3H, s), 3.45 (2H, m), 4.67 (1H, m), 5.21 (2H, s), 5.41 (1H, s), 6.49 (2H, broad s), 7.32 (5H, s).

The esters of Preparation F are converted to the corresponding 2-beta-aminocarbonyl derivatives in like manner.

EXAMPLE 18

Benzyl 2-beta-Cyano-2-alpha-Methyl-(5R)Penam-3-alpha-Carboxylate 1,1-Dioxide Pyridine (0.29 ml.) was added to a solution of benzyl 2-beta-aminocarbonyl-2-alpha-methyl-(5R)penam-3-alpha-carboxylate 1,1-dioxide (182 mg.) in chloroform (5 ml.) under a nitrogen atmosphere at 0° C. Phosphorous pentachloride (152 mg.) was then added and the mixture stirred at 0° C. for one-half hour. The mixture is then allowed to reach room temperature (about a half hour) after which ethyl acetate (20 ml.) and water (20 ml.) were added thereto. The pH is adjusted to 3.0 and the ethyl acetate phase separated and washed successively with aqueous acid (pH 3.0, 20 ml.), water (20 ml.) and brine (20 ml.) and then dried (Na$_2$SO$_4$). Removal of the ethyl acetate gave an oil to which chloroform (5 ml.) was added and then removed by evaporation in vacuo. Repetition of this step gave 166 mg. of the title product as an oil.

NMR (CDCl$_3$) δ 1.55 (3H, s), 3.58 (2H, m), 4.69 (1H, m), 5.08 (1H, s), 5.23 (2H, ABq), 7.32 (5H, s).

Dehydration of the remaining 2-beta-aminocarbonyl-2-alpha-methyl-(5R)penam-3-alpha-carboxylic acid 1,1- dioxide esters of Example 17 in like manner, provides the corresponding 2-beta-cyano-2-alpha-methyl-(5R)-penam-3-alpha-carboxylic acid 1,1-dioxide esters.

EXAMPLE 19

2-beta-Cyano-2-alpha-Methyl-(5R)Penam-3-alpha-Carboxylic Acid 1,1-Dioxide

Benzyl 2-beta-cyano-2-alpha-methyl-(5R)penam-3-alpha-carboxylate 1,1-dioxide (116 mg.) was hydrogenolyzed according to the procedure of Example 12 to give 80 mg. of the title acid.

NMR (Acetone-$d_6$, external tetramethyl silane standard) δ 1.89 (3H, s), 3.44 (1H, dd, J=2,16 Hz), 3.87 (1H, dd, J=4,16 Hz), 5.02 (1H, s), 5.14 (1H, dd, J=2,4 Hz).

EXAMPLE 20

Chloromethyl 2-beta-Carbomethoxy-2-alpha-Methyl-(5R)-Penam-3-alpha-Carboxylate 1,1-Dioxide To a mixture of 2-beta-carbomethoxy-2-alphamethyl-(5R)penam-3-alpha-carboxylic acid 1,1-dioxide (9.52 g.), methylene chloride (75 ml.) and water (25 ml.) is added, with stirring, 40% aqueous tetrabutylammonium hydroxide until the pH is 6.0. The layers are separated, and the aqueous phase extracted with further methylene chloride. The combined methylene chloride solutions are dried (Na$_2$SO$_4$) and concentrated in vacuo to give the tetrabutylammonium salt of 2-betacarbomethoxy-2-alpha-methyl-(5R)penam-3-alpha-carboxylic acid, as an oil.

The tetrabutylammonium salt and 50 ml. of chloroiodomethane are stirred at room temperature for ca. 18 hours, and the reaction mixture then concentrated in vacuo. The residue is chromatographed on silica gel using 1:1 ethyl acetate-hexane. The product containing fractions are combined and evaporated in vacuo, giving the title ester as a viscous oil.

In like manner the following compounds are prepared by substituting the appropriate 2-beta-substituted-2-alpha-methyl-(5R)penam-3-alpha-carboxylic acid for the 2-beta-carbomethoxy compound:

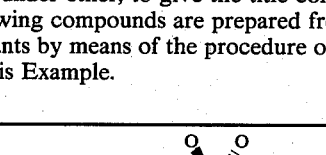

| R$_2$ | R$_2$ |
|---|---|
| COOC$_2$H$_5$ | COOCH$_2$CH$_2$OH |
| COO—n-C$_3$H$_7$ | COO(CH$_2$)$_3$OH |
| COO—i-C$_3$H$_7$ | COO(CH$_2$)$_4$OH |
| COO—n-C$_4$H$_9$ | COOCH$_2$CH(CH$_3$)CH$_2$OH |
| COOCH$_2$CH$_2$NHCOCH$_3$ | COOCH$_2$COOCH$_3$ |
| COO(CH$_2$)$_3$NHCOCH$_3$ | COOCH$_2$COOC$_4$H$_9$ |
| COO(CH$_2$)$_4$NHCOCH$_3$ | COCH$_3$ |
| CONH$_2$ | CN |
| CON(CH$_3$)$_2$ | |
| CON(CH$_3$) (n-C$_4$H$_9$) | |
| CON(n-C$_4$H$_9$)$_2$ | |
| CON(C$_2$H$_5$)$_2$ | |

EXAMPLE 21

The procedure of Example 20 is repeated, except that the chloroiodomethane used therein is replaced by an equimolar amount of bromoiodomethane, diiodomethane, di(methylsulfonyloxy)methane, di(isobutylsulfonyloxy)methane, di(phenylsulfonyl)methane, di(4-tolylsulfonyloxy)methane or 1-chloro-1-iodoethane. This affords the corresponding bromomethyl, iodomethyl, methylsulfonyloxymethyl, isobutylsulfonyloxymethyl, phenylsulfonyloxymethyl, 4-tolylsulfonyloxymethy, and 1-chloroethyl esters.

EXAMPLE 22

6'-(2-Azido-2-phenylacetamido)penicillanoyloxymethyl-2-beta-carbomethoxy-2-alpha-methyl-(5R)penam-3-alpha-carboxylate 1,1-Dioxide To a stirred solution of 1.4 g. of potassium 6-(2-azido-2-phenylacetamido)penicillanate in 20 ml. of dimethyl sulfoxide is added 1.02 g. of chloromethyl beta-carbomethoxy-2-alpha-methyl-(5R)penam-3-alphacarboxylate 1,1-dioxide followed by a few milligrams of sodium iodide. Stirring is continued overnight at ca. 25° C., and then the reaction mixture is poured into 140 ml. of ice-water. The pH is raised to 8.5, and the mixture extracted with ethyl acetate. The combined ethyl acetate extracts are washed with water, dried (Na$_2$SO$_4$) and evaporated in vacuo to give the crude title compound. It can be purified by chromatography on silica gel, eluting with a mixture of ethyl acetate and hexane.

EXAMPLE 23

6'-(2-Amino-2-Phenylacetamido)penicillanoyloxymethyl 2-beta-carbomethoxy-2-alpha-methyl-(5R)penam-3-alpha-carboxylate 1,1-Dioxide A mixture of 4.6 g. of 6'-(2-azido-2-phenylacetamido)penicillanoyloxymethyl 2-beta-carbomethoxy-2-alpha-methyl-(5R)penam-3-alpha-carboxylate 1,1-dioxide, 4.6 g. of 10% palladium-on-carbon, 30 ml. of dichloromethane and 30 ml. of isopropanol is shaken under an atmosphere of hydrogen, at ca. 3.52 kg/cm$^2$ (50 psig), for 1 hour. An additional 1.0 g. of 10% palladium-on-carbon is then added and the shaking under hydrogen at 3.52 kg/cm$^2$ (50 psig) is continued for 30 minutes. The reaction mixture is then filtered and the filtrate evaporated to dryness in vacuo. The residue is triturated under ether, to give the title compound.

The following compounds are prepared from appropriate reactants by means of the procedure of Example 22 and of this Example.

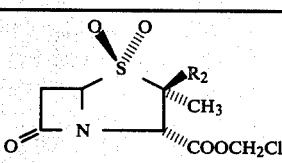
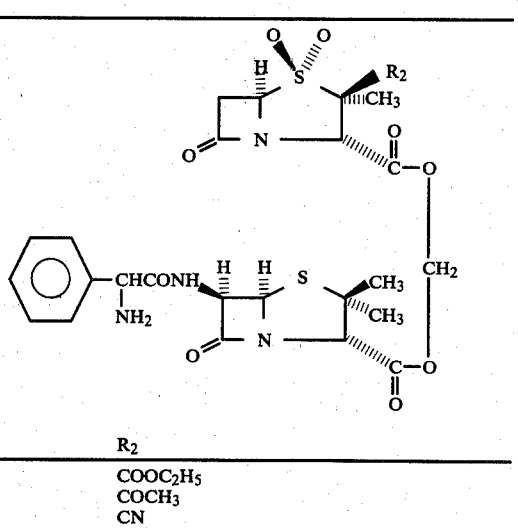

| R$_2$ |
|---|
| COOC$_2$H$_5$ |
| COCH$_3$ |
| CN |
| CON(CH$_3$)$_2$ |

-continued

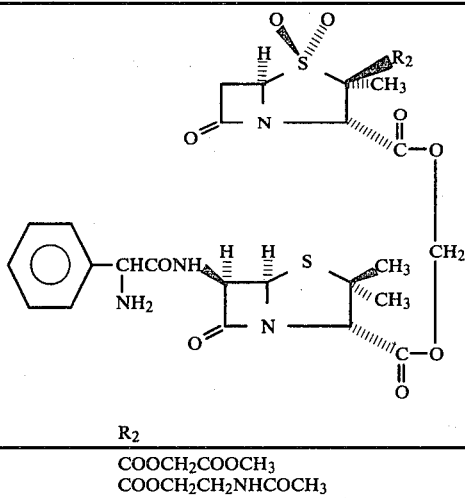

| R<sub>2</sub> |
|---|
| COOCH$_2$COOCH$_3$ |
| COOCH$_2$CH$_2$NHCOCH$_3$ |

EXAMPLE 24

6'-(2-Amino-2-[4-hydroxyphenyl]acetamido)penicillanoyloxymethyl 2-beta-carbomethoxy-2-alpha-methyl-(5R)penam-3-alpha-carboxylate 1,1-dioxide A mixture of 1.3 g. of 6'-(2-benzyloxycarbonylamino-2-[4-hydroxyphenyl]acetamido)penicillanoyloxymethyl 2-beta-carbomethoxy-2-alpha-methyl-(5R)penam-3-alpha-carboxylate 1,1-dioxide (from Preparation E), 0.7 g. of 6'-(2-benzyloxycarbonylamino-2-[4-benzyloxycarbonyloxyphenyl]acetamido)penicillanoyloxymethyl 2-betacarbomethoxy-2-alpha-methyl-(5R)penam-3-alpha-carboxylate 1,1-dioxide (from Preparation E), 30 ml. of dichloromethane, 30 ml. of isopropanol and 2.0 g. of 10% palladium-on-carbon is shaken under an atmosphere of hydrogen, at ca. 3.52 kg/cm$^2$ (50 psig), for 45 minutes. At this point, a further 2.0 g. of 10% palladium-on-carbon is added and the mixture shaken under hydrogen, at ca. 3.52 kg/cm$^2$ (50 psig), for a further 45 minutes. The step of adding an additional 2.0 g. of 10% palladium-on-carbon and rehydrogenation for 45 minutes is repeated 3 more times. The reaction mixture is then filtered and the filtrate evaporated to dryness in vacuo. The residue is triturated under ether.

PREPARATION A

Benzyl 2-beta-Chloroacetoxymethyl-2-alpha-Methyl-(5R)Penam-3-alpha-Carboxylate

A solution of chloroacetic anhydride (47.8 g.), 0.2795 mole) in toluene (300 ml.) was heated to vigorous reflux in a three-necked flask fitted with a distillation head, dropping funnel, and an inlet tube set below the surface of the toluene, said inlet tube being connected to a flask of boiling toluene so as to continually replace the toluene lost by distillation. After a half-hour of distillation, benzyl 2-alpha-, 2-beta-dimethyl(5R)penam 3-alpha-carboxylate 1-alpha-oxide (10.73 g., 0.0349 mole) in toluene (50 ml.) was added via the dropping funnel over a seven minute period. Distillation was continued for 15 minutes. The reaction mixture was allowed to cool, and the remaining toluene was removed by distillation in vacuo to give an oil. The oil was shaken up in ethyl acetate (300 ml.)-water (500 ml.) and the pH adjusted to 8.5 with 6 N NaOH. The phases were separated and the ethyl acetate washed once again with water (500 ml.) adjusted to pH 8.5, followed by water (1000 ml.), brine (500 ml.) and then dried (Na$_2$SO$_4$). Evaporation of the ethyl acetate in vacuo gave 14 g. of a dark oil which was purified by chromatography on silica gel using hexane ethyl acetate (2:1) as eluant. Title product rich fractions were combined and concentrated to an oil, which crystallized after dissolution in a small amount of ether/hexane with subsequent cooling and seeding to give 3.52 g.

NMR (CDCl$_3$) δ 1.39 (3H, s), 3.05 (1H, q, J=2, 16), 3.55 (1H, q, J=4, 16), 4.04 (2H, s), 4.12 (2H, q, J=11), 4.76 (1H, s), 5.15 (2H, s), 5.29 (1H, q, J=2, 4), 7.3 (5H, s).

PREPARATION B

Benzyl 2-beta-Hydroxymethyl-2-alpha-Methyl-(5R)-Penam-3-alpha-Carboxylate

Thiourea (2.44 g., 32.1 mmoles) was added to a solution of benzyl 2-beta-chloroacetoxymethyl-2-alpha-methyl-(5R)penam-3-alpha-carboxylate (4.11 g., 10.71 mmoles) in N,N-dimethylformamide (10 ml.) and pyridine (5 ml.) cooled in a ice bath. When solution of the thiourea was complete, the reaction mixture was warmed to room temperature in a water bath. Partial solidification of the reaction mixture occurred after one hour, and 5 ml. N,N-dimethylformamide was added to facilitate stirring. After stirring for a total of five hours the reaction mixture was poured into water (400 ml.)-ethyl acetate (200 ml.) and the pH adjusted to 3.0 by addition of dilute phosphoric acid. The phases were separated, the organic phase extracted again with water at pH 3 followed successively by washing with water (50 ml.) and brine (50 ml.). It was then dried (Na$_2$SO$_4$) and evaporated in vacuo to give an oil. The oil was taken up in ether (10 ml.), seeded and stirred to give 2.71 g. of crystalline product (82%).

NMR (CDCl$_3$) δ 1.3 (3H, s), 2.6 (1H, bs), 3.0 (1H, q, J=2, 16), 3.52 (1H, q, J=4, 16), 3.54 (2H, s), 4.84 (1H, s), 5.11 (2H, s), 5.28 (1H, q, J=2, 4), 7.26 (5H, s).

PREPARATION C

Benzyl 2-beta-Carboxy-2-alpha-Methyl-(5R)Penam-3-alpha-Carboxylate

To a solution of benzyl 2-beta-hydroxymethyl-2-alpha-methyl-(5R)penam-3-alpha-carboxylate (307 mg., 1 mmol) in N,N-dimethylformamide (4 ml.) under a nitrogen atmosphere and cooled in an ice-water bath was added pyridinium dichromate (1.37 g., 3.5 mmol) and the mixture stirred and cooled until the dichromate dissolved. The cooling bath was removed and the mixture stirred overnight at room temperature. It was then poured into water/ethyl acetate and the pH adjusted to 2.0. The ethyl acetate phase was separated, washed at pH 2.0 and then dried (Na$_2$SO$_4$) and evaporated in vacuo. The residue was taken up in ethyl acetate/water and the pH adjusted to 2.0. The ethyl acetate phase was separated then washed at pH 8.0, dried (Na$_2$SO$_4$) and evaporated in vacuo to give 68 mg. of crystalline product.

NMR (CDCl$_3$) δ 1.56 (3H, s), 3.34 (2H, m), 5.22 (2H, s), 5.33 (1H, s), 5.43 (1H, m), 7.38 (5H, s), 9.24 (1H, br).

PREPARATION D

Benzyloxycarbonyl Protection of 6-(2-Amino-2-[4-hydroxyphenyl]acetamido)penicillanic Acid To a stirred slurry of 39.0 g. of 6-(2-amino-2-[4-hydroxyphenyl]acetamido)penicillanic acid trihydrate in 500 ml. of water and 300 ml. of acetone was added 6 N sodium hydroxide to give a stable pH of 8.2. To the solution so obtained was added 13.6 ml. of benzyloxycarbonyl chloride, dropwise, with stirring, during 30 minutes, with the pH being maintained between 7.0 and 8.0 by the simultaneous addition of 6 N sodium hydroxide. Stirring and addition of sodium hydroxide was continued until the pH stabilized at 7.5., and then the mixture was extracted three time with ether. To the aqueous phase was added 300 ml. of ethyl acetate, and the pH was lowered to 2.0. The ethyl acetate layer was removed, and the aqueous phase was further extracted with ethyl acetate. The combined ethyl acetate solutions were washed with water, dried ($Na_2SO_4$) and concentrated in vacuo to give 47.2 g. of a foam. Examination of this product showed that it was 6-(2-benzyloxycarbonylamino-2-[4-hydroxyphenyl]acetamido)-penicillanic acid, contaminated with some 6-(2-benzyloxycarbonylamino-2-[4-benzyloxycarbonyloxyphenyl]acetamido)penicillanic acid.

PREPARATION E

Reaction of Benzyloxycarbonyl-protected 6-(2-Amino-2-[4-hydroxyphenyl]acetamidopenicillanic Acid with Chloromethyl 2-beta-carbomethoxy-2-alpha-methyl-(5R)penam-3-alpha-carboxylate 1,1-Dioxide To a stirred mixture of 5.0 g. of the product of Preparation D, 75 ml. of dichloromethane and 25 ml. of water is added 40% aqueous tetrabutylammonium hydroxide, until a stable pH of 8.0 is achieved. The layers are separated and the aqueous layer washed with dichloromethane. The combined dichloromethane solutions are evaporated in vacuo to a yellow foam.

A mixture of the above 5.0 g. of yellow foam, 1.36 g. of iodomethyl 2-beta-carbomethoxy-2-alpha-methyl-(5R)penam-3-alpha-carboxylate 1,1-dioxide and 30 ml. of acetone is stirred for 5 minutes. The reaction medium is evaporated in vacuo, and the residue chromatographed on 500 g. of silica gel, eluting with 60:40 ethyl acetate-dichloromethane.

The fractions containing the less polar product are combined and evaporated in vacuo to give 6'-(2-[benzyloxycarbonylamino]-2-[4-benzyloxycarbonyloxyphenyl]acetamido)penicillanoyloxymethyl 2-beta-carbomethoxy-2-alpha-methyl-(5R)penam-3-alpha-carboxylate 1,1-dioxide as a yellow foam.

The fractions containing the more polar product are combined and evaporated in vacuo to a pale yellow foam: 6'-(2-[benzyloxycarbonylamino]-2-[4-hydroxyphenyl]acetamido)penicillanoyloxymethyl 2-beta-carbomethoxy-2-alpha-methyl-(5R)penam-3-alpha-carboxylate 1,1-dioxide.

PREPARATION F

Following the procedure of Example E, the 2-beta-substituted-2-alpha-methyl-(5R)penam-3-alpha-carboxylic acid 1,1-dioxides of Examples 4, 6, 8, 10, 12, 14, 16 and 19 are converted to their tetrabutylammonium salts, and said salts then reacted with the iodide derivative of the appropriate readily hydrolyzable ester, e.g., 3-phthalidyl iodide, 4-crotonolactonyl iodide, gamma-butyrolacton-4-yl iodide, $I-C(R_3)(R_4)O-CO-R_5$ wherein $R_3$, $R_4$ and $R_5$ are as previously defined.

The readily hydrolyzable esters of said 2-beta-substituted-2-alpha-methyl-(5R)penam-3-alpha-carboxylic acid 1,1-dioxides thus prepared are:
3-phthalidyl
4-crotonolactonyl
γ-butyrolacton-4-yl
acetoxymethyl
1-acetoxyethyl
hexanoyloxymethyl
1-isobutyryloxyethyl
pivaloyloxymethyl

I claim:
1. A compound having the formula

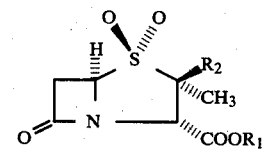

wherein $R_1$ is selected from the group consisting of
(a) hydrogen;
(b) ester forming residues readily hydrolyzable in vivo selected from the group consisting of
(1) 3-phthalidyl, 4-crotonolactonyl and gamma-butyrolacton-4-yl;

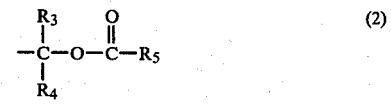

(2)

wherein each of $R_3$ and $R_4$ is selected from the group consisting of hydrogen and methyl; and $R_5$ is selected from the group consisting of alkyl having from 1 to 5 carbon atoms and alkoxy having from 1 to 5 carbon atoms; and

(3)

wherein each of $R_3$ and $R_4$ is selected from the group consisting of hydrogen and methyl;

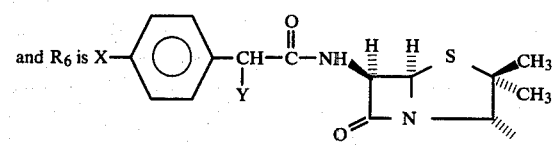

and $R_6$ is wherein X is selected from the group consisting of hydrogen and hydroxy; and Y is selected from the group consisting of azido and amino;
(c) carboxy protecting group selected from the group consisting of benzyl and 4-nitrobenzyl; $R_2$ is selected from the group consisting of CN and CO-Z; Z is selected from the group consisting of alkoxy having from 1 to 4 carbon atoms; omega-hydroxyalkoxy having from 2 to 4 carbon atoms; carboalkoxymethoxy having from 3 to 6 carbon atoms; dialkylamino wherein each alkyl group has from 1 to 4 carbon atoms; omega-acetamidoalkoxy having from 2 to 4 carbon atoms in the alkoxy group, and methyl; or a pharmaceutically-acceptable base salt of those compounds wherein R₁ is hydrogen; or a pharmaceutically-acceptable acid addition salt of those compounds wherein Y is amino.

2. A compound according to claim 1 wherein R₁ is hydrogen.

3. A compound according to claim 2 wherein R₂ is CO-Z wherein Z is alkoxy.

4. The compound according to claim 3 wherein Z is methoxy.

5. A compound according to claim 2 wherein R₂ is CO-Z wherein Z is carboalkoxymethoxy.

6. The compound according to claim 5 wherein Z is carbomethoxymethoxy.

7. The compound according to claim 2 wherein R₂ is CN.

8. A compound having the formula

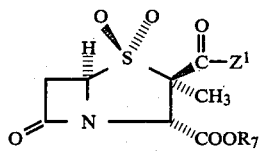

wherein Z¹ is selected from the group consisting of amino, chloro, hydroxy and OM wherein M is selected from the group consisting of sodium, potassium, ammonium and n-tetrabutylammonium; and R₇ is selected from the group consisting of benzyl and 4-nitrobenzyl.

9. A beta-lactam antibiotic effectiveness enhancing composition which comprises a pharmaceutically-acceptable carrier and a compound of the formula

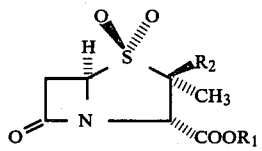

wherein R₁ is selected from the group consisting of
(a) hydrogen;
(b) ester forming residues readily hydrolyzable in vivo selected from the group consisting of
(1) 3-phthalidyl, 4-crotonolactonyl and gamma-butyrolacton-4-yl;

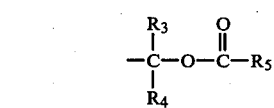

wherein each of R₃ and R₄ is selected from the group consisting of hydrogen and methyl; and R₅ is selected from the group consisting of alkyl having from 1 to 5 carbon atoms and alkoxy having from 1 to 5 carbon atoms; and

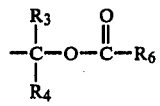

wherein each of R₃ and R₄ is selected from the group consisting of hydrogen and methyl;

and R₆ is 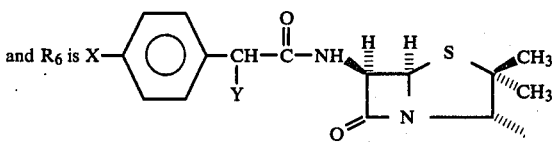

wherein X is selected from the group consisting of hydrogen and hydroxy; and Y is selected from the group consisting of azido and amino; R₂ is selected from the group consisting of CN and CO-Z; Z is selected from the group consisting of alkoxy having from 1 to 4 carbon atoms; omega-hydroxyalkoxy having from 2 to 4 carbon atoms; carboalkoxymethoxy having from 3 to 6 carbon atoms; dialkylamino wherein each alkyl group has from 1 to 4 carbon atoms; omega-acetamidoalkoxy having from 2 to 4 carbon atoms in the alkoxy group, and methyl; or a pharmaceutically-acceptable base salt of those compounds wherein R₁ is hydrogen; or a pharmaceutically-acceptable acid addition salt of those compounds wherein Y is amino.

10. A composition according to claim 9 wherein R₁ is hydrogen.

11. The composition according to claim 10 wherein R₂ is CO-Z wherein Z is methoxy.

12. A method of increasing the effectiveness of a beta-lactam antibiotic in a mammal which comprises co-administering with said beta-lactam antibiotic to said mammal a beta-lactam antibiotic effectiveness increasing amount of a compound of the formula

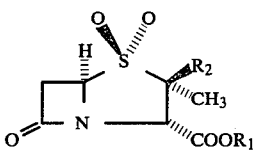

wherein R₁ is selected from the group consisting of
(a) hydrogen;
(b) ester forming residues readily hydrolyzable in vivo selected from the group consisting of
(1) 3-phthalidyl, 4-crotonolactonyl and gamma-butyrolacton-4-yl;

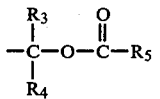

wherein each of R₃ and R₄ is selected from the group consisting of hydrogen and methyl; and R₅ is selected from the group consisting of alkyl having from 1 to 5 carbon atoms and alkoxy having from 1 to 5 carbon atoms; and

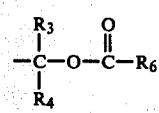
(3)

wherein each of $R_3$ and $R_4$ is selected from the group consisting of hydrogen and methyl;

and $R_6$ is 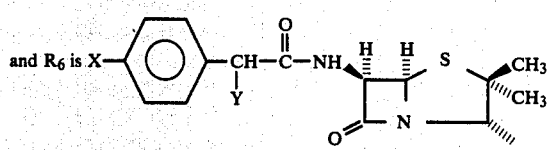

wherein X is selected from the group consisting of hydrogen and hydroxy; and Y is selected from the group consisting of azido and amino; $R_2$ is selected from the group consisting of CN and CO-Z; Z is selected from the group consisting of alkoxy having from 1 to 4 carbon atoms; omega-hydroxyalkoxy having from 2 to 4 carbon atoms; carboalkoxymethoxy having from 3 to 6 carbon atoms; dialkylamino wherein each alkyl group has from 1 to 4 carbon atoms; omega-acetamidoalkoxy having from 2 to 4 carbon atoms in the alkoxy group, and methyl; or a pharmaceutically-acceptable base salt of those compounds wherein $R_1$ is hydrogen; or a pharmaceutically-acceptable acid addition salt of those compounds wherein Y is amino.

13. A method according to claim 12 wherein $R_1$ is hydrogen.

14. The method according to claim 13 wherein $R_2$ is CO-Z wherein Z is methoxy.

* * * * *